United States Patent [19]

Bhardwaj et al.

[11] Patent Number: 5,578,316
[45] Date of Patent: Nov. 26, 1996

[54] PALATABLE PHARMACEUTICAL COMPOSITIONS

[75] Inventors: Sanjay Bhardwaj, Randolph, N.J.; Marshall Hayward, Weybridge, United Kingdom

[73] Assignee: SmithKline Beecham Corporation, Philadelphia, Pa.

[21] Appl. No.: 347,325

[22] PCT Filed: Jun. 4, 1993

[86] PCT No.: PCT/US93/05423

§ 371 Date: Feb. 15, 1995

§ 102(e) Date: Feb. 15, 1995

[87] PCT Pub. No.: WO93/24109

PCT Pub. Date: Dec. 9, 1993

Related U.S. Application Data

[63] Continuation of Ser. No. 893,288, Jun. 4, 1992, abandoned.
[51] Int. Cl.$^6$ .............. A61K 9/22; A61K 9/32; A61K 9/58
[52] U.S. Cl. .......... 424/441; 424/497; 424/482; 424/464
[58] Field of Search .................. 424/464, 497, 424/441, 482

[56] References Cited

U.S. PATENT DOCUMENTS

| | | | |
|---|---|---|---|
| 4,800,087 | 1/1989 | Mehta | 424/497 |
| 4,892,740 | 1/1990 | Takasima et al. | 424/474 |
| 4,925,675 | 5/1990 | Giannini et al. | 424/469 |
| 5,075,114 | 12/1991 | Roche | 424/470 |
| 5,084,287 | 1/1992 | Ghebre-Sellassie et al. | 424/495 |
| 5,112,621 | 5/1992 | Stevens et al. | 424/497 |

Primary Examiner—James M. Spear
Attorney, Agent, or Firm—William T. King; Stuart R. Suter; Edward T. Lentz

[57] ABSTRACT

A pharmaceutical granular composition and method are provided for masking the taste of unpleasant tasting drugs, wherein drug cores are coated with separate layers of aqueous dispersions of methacrylate ester copolymers, preferably, poly(ethylacrylate, methyl methacrylate) to which quaternary ammonium groups have been introduced to modify the permeability of the ester. Additionally, the coating composition may contain plasticizers and conventional excipients. The coating system releases drug by diffusion and is influenced by drug solubility and media pH. The coated pharmaceutical granules of the invention can be used to prepare chewable tablets with good palatability and bioavailability.

30 Claims, No Drawings

PALATABLE PHARMACEUTICAL COMPOSITIONS

This is a continuation of U.S. Ser. No. 07/893,288 filed 4 Jun. 1992, now abandoned.

This invention relates to a composition and method for taste masking bitter, unpleasant tasting medicaments and provides for an immediate release of the medicament after ingestion. More specifically, the invention relates to medicament cores coated with methacrylate ester copolymers which masks the bitter and unpleasant taste of the medicament. A method of preparing dosage units such as chewable tablets, employing the coated medicament is also described.

In a preferred embodiment of this invention, the composition comprises a chewable tablet containing cimetidine coated with separate layers of methacrylate ester copolymers. The tablets do not exhibit the bitter taste of cimetidine and provides for an immediate release of the cimetidine.

BACKGROUND OF THE INVENTION

Cimetidine is a histamine $H_2$-antagonist which has been shown to be useful in the treatment of duodenal, gastric, recurrent and stomal ulceration. It is also employed in the management of patients who are at high risk from hemorrhage of the upper gastrointestinal tract.

Cimetidine is known to be one of many medicaments to have a pronounced bitter taste. This is not usually a problem when the dosage form employed is a capsule or a tablet designed to be swallowed, thereafter to disintegrate upon reaching the stomach. However, such dosage forms can be impractical when it is desired to administer a large amount of active ingredient, or to co-administer a relatively bulky second active ingredient such as an antacid or alginate. Moreover, many individuals have difficulty in swallowing a solid dosage form A conventional approach to administering relatively large amounts of active ingredient in a solid dosage form is by means of a chewable tablet, i.e., a tablet which disintegrates in the mouth upon being chewed. Such a tablet also circumvents the problem of a solid dosage being difficult to swallow.

It will be appreciated that a major requirement of such a dosage form is that it must be palatable, since an unpalatable formulation increases the risk of a patient neglecting to take the tablet. Such non-compliance with the dosing regimen will in turn delay or prevent the patient's recovery from the condition under treatment.

A further requirement of such a composition is that once the disintegrated tablet reaches the stomach, the individual particles should release the active ingredient rapidly and completely in order to ensure that substantially all of the active ingredient is absorbed; that is to say the formulation should be readily bioavailable.

In the case of cimetidine, because of its bitterness and solubility characteristics, the provision of such a dosage form represents a considerable problem.

Several solutions to the problem of taste masking pharmaceutical compositions have been attempted. For example, cimetidine granules have been coated with various compositions such as ethylcellulose and polyvinyl and acrylic polymers. One such proposal is disclosed in U.S. Pat. No. 4,800,087 wherein a polymer mixture coating is employed. The mixture comprises a high temperature film forming copolymer of polymethyacrylic acid ester and acrylic acid ester and a low temperature film forming copolymers consisting of methacrylic acid ester and styrene acrylate. U.S. Pat. No. 4,892,740 discloses pharmaceutical preparations having improved flavouring characteristics obtained by the drug being coated by a polymeric substance which is soluble in gastic juice.

DESCRIPTION OF THE INVENTION

In accordance with this invention it has been unexpectedly discovered that when bitter, unpleasant tasting medicaments are coated with separate layers of specific methacrylate ester copolymers a core results which is palatable and has good dissolution characteristics in the stomach. The coated core results in a taste masked medicament without reducing its bioavailability.

The core particles which are to be coated can be composed of pure granular drug material or drug granules prepared in the conventional manner employing appropriate binding agents. The particle size of the core material is from about 180 to 420 microns. This range is preferable because larger particles tend to be ruptured during chewing and smaller particles present problems in the coating process. The particles should possess adequate hardness and friability characteristics to withstand attritive forces during the coating operation.

Exemplary of bitter, unpleasant tasting drugs applicable to the taste-masking compositive of this invention are histamine $H_2$-antagonists, such as, for example, cimetidine, ranitidine, famotidine, nizatidine, etinidine, lupitidine, nifentidine, niperotidine, roxatidine, sulfotidine, tuvatidine and zaltidine; antibiotics, such as penicillin, ampicillin and erythromycin, acetaminophen; caffeine, dextromethorphan, diphenhydramine, theophylline, spironolactone and chloropheniramine. The above drugs are not limiting but merely exemplary of unpleasant tasting drugs that may be employed in this invention.

In a preferred embodiment the taste masking compositions of this invention will contain cimetidine or caffeine.

When, cimetidine is employed the composition will contain from about 75 mg to 800 mg. Preferably it will containing from about 100 mg. to 400 mg. of cimetidine.

The coating material is selected from the wide range of copolymers available under the tradename of Eudragits. These copolymers are manufactured and marketed by R öhm Pharma of Darmstadt, Gemany. Preferably, the coating composition is comprised of aqueous dispersions of ethyl acrylate (EA) and methyl methacrylate (MMA). A particularly preferred coating composition of this invention is an aqueous dispersion of poly(EA—MMA) to which hydrophilic quaternary ammonium groups have been introduced to modify the permeability of the ester. Copolymerization of the above poly(EA—MMA)ester with different ratios of trimethylammonioethyl methacrylate chloride (TAMCl) results in methacrylic ester copolymers of either high or low permeability. For example, a coating film of high permeability results when poly (EA—MMA—TAMCl) are present in a 1:2:0.2 ratio. This copolymer is available under the tradename of Eudragit RL30D. A coating film of low permeability results when poly (EA—MMA—TAMCl) are present in a ratio of 1:2:0.1. This product is available under the tradename of Eudragit RS30D. Both Eudragit RL30D and RS30D are sold as 30% aqueous dispersions.

The polymeric aqueous dispersions may also contain additives such as, plasticizers, pigments, talc and the like. Plasticizers are employed to assist in the film forming characteristics of the polymeric coating and also to provide greater integrity and elasticity to the films coat. Exemplary of plasticizers that may be employed in the coatings of this invention are triethyl citrate, triacetin, tributyl citrate, acetyl triethyl citrate, acetyl tributyl citrate, dibutyl phthalate, dibutyl sebacate, vinyl pyrrolidone and propylene glycol. The amount of plasticizer present in the aqueous dispersion may be from 5% to about 30%. Preferably, the plasticizer will be present in an amount of from about 15% to about 25% by weight of the dry polymers.

Exemplary of pigments employed in the polymeric coating solutions of the invention may be color pigments such as FD&C or D&C approved lakes and dyes, iron oxide and titanium dioxide. The amount of pigment present in the coating solution may be from about 1% to about 20% by weight of the dry polymer.

The method of coating the granular core particles comprises applying aqueous dispersions of Eudragit RL30D and RS30D to the core as distinct layers in subsequent coating steps. The polymers will be present in the dispersions in an amount of from about 10% to about 30% as the dry polymer. Advantageously, the core material is coated by subjecting them to air suspension coating technique. Preferably a Glatt Fluid Bed Wurster Coater is employed. An inner coating is applied by spraying (bottom spray) onto the fluidizing drug cores an aqueous dispersion of RL30D. The spraying is continued until a theoretical weight gain of from about 25% to about 50% of the batch is obtained. The coated material is retrieved and dedusted on a #60–80 U.S. mesh screen, equivalent to approximately 180–250 microns.

A second coating layer comprising an aqueous dispersion of RS30D is applied to the above coated, dedusted particles to a theoretical weight gain of from about 5% to about 15% of the original batch. When the coating run is completed the particles are again dedusted using a #80 mesh screen resulting in a final product having a particle size of from about 200 to about 400 microns.

The dedusting between coating steps is preferable particularly when friable drug particles are employed. More important, the dedusting steps result in a drug particle size which contributes to the immediate release and bioavailability characteristics of the coated drug granules.

One of the advantages of the coated drug particles of this invention is that they provide a method for formulating extremely palatable solid dosage units which contain unpleasant tasting drugs. For example, orally administrable dosage units such as chewable tablets, troches, lozenges or sprinkle formulations may be prepared from the coated granules of this invention. The granules of the present invention are particularly suitable for use in preparing chewable tablets.

Where the dosage unit is a chewable tablet, conventional pharmaceutical excipients in addition to the coated core may be included. For example, fillers, lubricants, binders, compression aids, and wetting agents may be employed. The fillers may be water soluble or insoluble such as lactose, sucrose or terra alba. Typical lubricants are stearic acid and its pharmaceutically acceptable alkali metal salts. Examples of binders are polyvinylpyrrolidones, polyethylene glycol, natural gums including veegum, tragacanth, acacia and gelatin. Exemplary of wetting agents include sodium lauryl sulfate, polysolbates and polyoxyethylene surfactants. Starch, alginates and their salts and maize would be representative of disintegrants. Typical compression aids would be microcrystalline cellulose, dicalcium phosphate and compressible sugar. To further assist patient compliance, the tablet can also contain sweeteners such as aspartame, sodium cyclamate and sodium saccharinate and flavorants such as orange, mint, cola, strawberry and the like.

The invention is illustrated but in no way limited by the following examples.

EXAMPLE 1

| Eudragit RL30D - Inner Coating Solution | |
| --- | --- |
| Ingredients | Amount/Gms |
| Eudragit RL30D (dry polymer) | 160.00 |
| Triethyl Citrate | 32.00 |
| Talc | 1.60 |
| Yellow #6 Lake | 1.60 |
| Distilled Water | 768.00 |

To 533.33 gms of a 30% aqueous dispersion of Eudragit RL30D (equivalent to 160.00 gms of dry polymer) was added the triethyl citrate with gentle mixing. The talc and lake were then added with low shear mixing. The distilled water was added and slowly mixed with the suspension.

| Eudragit RS30D Outer Coating Solution | |
| --- | --- |
| Ingredients | Amount/Gms. |
| Eudragit RS30D (dry polymer) | 40.00 |
| Triethyl citrate | 8.00 |
| Yellow #6 Lake | 0.40 |
| Talc | 0.40 |
| Distilled Water | 192.00 |

To 133.33 gms of a 30% aqueous dispersion of RS30D (equivalent to 40.00 gms of dry polymer) the ingredients were added and mixed following the above procedure.

Preparation of Coated Granules

Employing a Glatt Fluid Bed Wurster Coater, 400 mg of caffeine having a size of from about 180 to 420 microns were fluidized. Onto the fluidizing caffeine a first coating of the above Eudragit RL30D aqueous dispersion was applied by the bottom spray until a 40% weight gain of the batch was obtained. The batch was retrieved and dedusted on a #60 mesh screen to remove the fines. The sifted coated particles were then returned to the Wurster chamber and a second coating of the above RS30D aqueous dispersion was applied by the bottom spray until a 10% weight gain of the original batch was achieved. The coated particles were then removed, dedusted on a #60 mesh screen resulting in a final particle size of 200 to 400 microns.

| Preparation of Chewable Tablet | |
| --- | --- |
| Ingredients | Amount/mg |
| Caffeine coated beads* | 400.00 |
| Compressible Sugar N.F. | 1595.00 |
| Magnesium Stearate | 500.00 |

*Equivalent to 200 mg. of Caffeine

The ingredients were thoroughly mixed and directly compressed employing the appropriate punches and dies.

| Eudragit RL30D - Inner Coating Solution | |
|---|---|
| Ingredients | Amount/Gms. |
| Eudragit RL 30D (dry polymer) | 248.00 |
| Triethyl citrate | 49.60 |
| Talc | 2.48 |
| Distilled Water | 1121.78 |

To 826.67 g of a 30% aqueous dispersion of Eudragit RL 30D (equivalent to 248.00 g of dry polymer) was added the triethyl citrate with gentle mixing. The talc was then added with low shear mixing. The distilled water was added and slowly mixed with the suspension.

| Eudragit RS 30D - Outer Coating Solution | |
|---|---|
| Ingredients | Amount/Gms. |
| Eudragit RS 30D (dry polymer) | 62.00 |
| Triethyl citrate | 12.40 |
| Yellow #6 Lake | 0.62 |
| Talc | 0.62 |
| Distilled Water | 283.96 |

To 206.67 g of a 30% aqueous dispersion of RS 30D (equivalent to 62.00 g of dry polymer) was added the triethyl citrate with gentle mixing. The talc and lake were then added with low shear mixing. The distilled water was added and slowly mixed with the suspension.

Preparation of Coated Granules

Employing a Glatt Fluid Bed Wurster Coater, 600.0 gms of cimetidine having a size of from about 250 to 177 microns were fluidized. Onto the fluidized cimetidine a first coating of the above Eudragit RL 30D aqueous dispersion was applied by the bottom spray to obtain a target weight gain of 40%. The batch was retrieved and sieved on a #60 mesh screen to remove the fines. The sifted coated particles were then returned to the Wurster chamber and a second coating of the above RS 30D aqueous dispersion was applied by the bottom spray to obtain a target weight gain of 10% of the original batch. The coating particles were then removed, dedusted on a #60 mesh screen resulting in a final particle size of about 200 to 400 microns.

| Preparation of Chewable Tablet | |
|---|---|
| Ingredients | Amount in Milligrams |
| Cimetidine coated granules* | 161.0 |
| Compressible Sugar N.F. | 1829.0 |
| Magnesium Stearate | 10.0 |

*Equivalent to 100.0 mg of Cimetidine

The ingredients were thoroughly mixed and directly compressed employing the appropriate punches and dies.

Unexpectedly, it has been discovered that when the polymers RL30D and RS30D are applied as distinct coating layers as described hereinabove they not only produce extremely palatable granules which significantly minimizes the unpleasant taste associated with bitter drugs but also result in an immediate release of the drug in the stomach. This is surprising because both polymers are employed to produce either a sustained release or an enteric coated effect of the drug.

A further advantage of this invention is that by employing an aqueous based coating medium the dangers associated with organic solvents, such as, for example, flammability, toxicity and pollution of the environment are eliminated.

The coating system of this invention releases the drug by diffusion and not explosion. The release is influenced by drug solubility and media pH.

What is claimed is:

1. A taste masked pharmaceutical granule composition for oral administration comprising a core material containing an unpleasant tasting drug said core having an inner polymeric coating of high permeability comprising poly(ethyl acrylate-methyl methacrylate) trimethylammonio ethyl methacrylate chloride in a 1:2:0.2 ratio and a outer polymeric coating of low permeability comprising poly(ethyl acrylate-methyl methacrylate) trimethylammonio ethyl methacrylate chloride in a 1:2:0.1 ratio said coating providing an immediate release of the drug in the stomach wherein said core material has an initial particle size of from about 180 to about 420 microns, and said coated granules of the granule composition have a final particle size of from about 200 to about 400 microns.

2. The composition of claim 1 wherein the inner polymeric coating contains a plasticizer.

3. The composition of claim 2 wherein the plasticizer is present in an amount of from about 5% to about 30% by weight of dry polymer.

4. The composition of claim 1, wherein said drug is selected from the group consisting of cimetidine, ranitidine, caffeine, acetaminophen, dextromethorphan, chlorpheniramine, diphenhydramine, theophylline, penicillin, ampicillin and erythromycin.

5. A chewable tablet containing the pharmaceutical granule composition of claim 1 and optionally further contains a pharmaceutical excipient.

6. A chewable tablet containing the granule composition of claim 4.

7. The chewable tablet of claim 6 wherein the drug is cimetidine and it is present in an amount of from about 100 mg to about 400 mg.

8. A method for preparing a taste masked pharmaceutical granule composition which comprises spraying onto a fluidized bed of a drug core material an aqueous dispersion of an inner polymeric coating of high permeability, retrieving and dedusting the coated core material and applying to a fluidized bed of the dedusted material an aqueous dispersion of an outer polymeric coating of low permeability dedusting and drying the coated particles wherein the inner polymeric coating is poly(ethylacrylate-methyl methacrylate) trimethylammonio ethyl methacrylate chloride in a 1:2:0.2 ratio and the outer polymeric coating is poly(ethylacrylate methylmethacrylate)trimethylammonio ethyl methacrylate chloride in a 1:2:0.1 ratio and the coated material is dedusted to a final particle size of from about 200 to about 400 microns.

9. The method of claim 8 wherein the drug is selected from the group consisting of cimetidine, ranitidine, caffeine, acetaminophen, dextromethorphan, chlorpheniramine, diphenhydramine, theophylline, penicillin, ampicillin and erythromycin.

10. The composition of claim 2 wherein said drug is selected from the group consisting of cimetidine, ranitidine, caffeine, acetaminophen, dextromethorphan, chlorpheniramine, diphenhydramine, theophylline, penicillin, ampicillin and erythromycin.

11. A taste masked pharmaceutical granule composition for oral administration comprising a core material, having an initial particle size of from about 180 to about 420 microns, containing a unpleasant tasting drug said core having an inner polymeric coating of high permeability comprising poly(ethyl acrylate-methyl methacrylate) trimethylammonio ethyl methacrylate chloride in a 1:2:0.2 ratio present in an amount of about 25 to about 50% dry net weight gain over the core and having an outer polymeric coating of low permeability comprising poly(ethyl acrylate-methyl methacrylate) trimethylammonio ethyl methacrylate chloride in a 1:2:0.1 ratio present in an amount of about 5 to about 15% dry net weight gain over the inner coated particle, said outer coating providing an immediate release of the drug in the stomach, said coated granules of the granule composition have a final particle size of from about 200 to about 400 microns.

12. A chewable tablet containing the granule composition of claim 10.

13. The method according to claim 8 wherein the inner polymeric coating optionally contain a plasticizer, and further wherein the outer inner polymeric coating optionally contain a plasticizer.

14. The method according to claim 8 wherein the granules are made into a chewable tablet.

15. The composition of claim 1 wherein the outer polymeric coating contains a plasticizer.

16. The composition of claim 15 wherein the plasticizer is present in an amount of from about 5% to about 30% by weight of dry polymer.

17. The composition of claim 1 wherein the inner polymeric coating is present in an amount of about 25 to about 50% dry net weight gain over the core.

18. The composition of claim 1 wherein the outer polymeric coating is present in an amount of about 5 to about 15% dry net weight gain over the inner coated particle.

19. The composition of claim 11 wherein said drug is selected from the group consisting of cimetidine, ranitidine, caffeine, acetaminophen, dextromethorphan, chlorpheniramine, diphenhydramine, theophylline, penicillin, ampicillin and erythromycin.

20. The composition of claim 11 wherein the inner polymeric coating contains a plasticizer.

21. The composition of claim 11 wherein the outer polymeric coating contains a plasticizer.

22. The composition of claim 20 wherein the plasticizer is present in an amount of from about 5% to about 30% by weight of dry polymer.

23. The composition of claim 21 wherein the plasticizer is present in an amount of from about 5% to about 30% by weight of dry polymer.

24. The method according to claim 9 wherein the drug is cimetidine or caffeine.

25. The method according to claim 8 wherein the core material has an initial particle size of from about 180 to about 420 microns.

26. The method according to claim 8 wherein the inner polymeric coating is present in an amount of about 25 to about 50% dry net weight gain over the core.

27. The method according to claim 8 wherein the outer polymeric coating is present in an amount of about 5 to about 15% dry net weight gain over the inner coated particle.

28. A chewable tablet containing the granule composition of claim 19.

29. The method according to claim 13 wherein the plasticizer is present in an amount of from about 5% to about 30% by weight of dry polymer.

30. The method according to claim 26 wherein the first dedusting has a core particle size of about 180 to 250 microns.

* * * * *